(12) United States Patent
Kirjavainen

(10) Patent No.: US 6,711,267 B1
(45) Date of Patent: Mar. 23, 2004

(54) METHOD AND APPARATUS FOR PROCESSING SOUND

(75) Inventor: Kari Kirjavainen, Espoo (FI)

(73) Assignee: Panphonics Oy, Tampere (FI)

( * ) Notice: Subject to any disclaimer, the term of this patent is extended or adjusted under 35 U.S.C. 154(b) by 0 days.

(21) Appl. No.: 09/308,442

(22) PCT Filed: Nov. 27, 1997

(86) PCT No.: PCT/FI97/00734

§ 371 (c)(1),
(2), (4) Date: May 19, 1999

(87) PCT Pub. No.: WO98/24088

PCT Pub. Date: Jun. 4, 1998

(30) Foreign Application Priority Data

Nov. 27, 1996 (FI) .................................................. 964717
Feb. 4, 1997 (FI) .................................................. 970475

(51) Int. Cl.[7] .......................... A61F 11/06; G10K 11/16; H03B 29/00
(52) U.S. Cl. ......................................... 381/71.1; 381/57
(58) Field of Search ........................ 381/71.1, 96, 71.6, 381/95, 56, 57, 58, 59

(56) References Cited

U.S. PATENT DOCUMENTS 5,018,203 A    5/1991    Sawyers et al.
5,402,496 A    3/1995    Soli et al.

FOREIGN PATENT DOCUMENTS

GB    1530814    11/1978
GB    2160070    12/1985

*Primary Examiner*—Minsun Oh Harvey
(74) *Attorney, Agent, or Firm*—Marshall, Gerstein & Borun LLP

(57) ABSTRACT

The invention relates to a method and an apparatus for sound processing, where sound is attenuated by measuring it and by producing with an actuator a sound field of opposite sign in view of the original sound field. A desired value signal (I) is supplied to the actuator which reproduces the signal. To the actuator is attached a sensor, measuring sound pressure, and the difference of the sensor signal (B) and the desired value signal (I) is applied as high gain feedback to the actuator. As a consequence, sound not pertaining to the desired value signal (I) can be attenuated in a simple manner, and sound in accordance with the desired value signal (I) can be produced simultaneously with the same apparatus.

19 Claims, 5 Drawing Sheets

METHOD AND APPARATUS FOR PROCESSING SOUND

The invention relates to a method for processing sound, in which method a sound field of an ambient sound is measured; a sound field of opposite sign in relation to the sound field of the ambient sound is produced by an actuator; a desired value signal is further applied to an actuator and a sound pressure of the ambient sound is measured with a sensor attached to the actuator, and the difference of the sensor signal and the desired value signal is applied to the actuator, and sound is produced in accordance with the desired value signal, and ambient sound not pertaining to the desired value signal is simultaneously attenuated.

The invention further relates to an apparatus for sound processing, the apparatus comprising an acoustic actuator, a sensor for measuring sound pressure attached thereto, means for applying a desired value signal to the actuator, and means for applying to the actuator the difference of the sound pressure, measured with a sensor, and the desired value signal.

It is known to attenuate sound with such a method that the sound pressure of a sound field and the particle velocity are measured, and on the basis of the measuring results actuators, in other words, means for producing attenuation sound are controlled in order to produce a sound field which is otherwise exactly the same as the original sound field, but of the opposite sign. As a consequence the sound field can be completely suppressed by means of the actuators. The method is applicable to sound attenuation, but production of a desired sound requires separate, complicated solutions.

German Patent Publication 3 025 391 discloses a method and an apparatus, in which sound is attenuated by measuring the sound field and by producing a sound field of opposite sign in relation to the original sound field. The supply of a desired value signal through a sound attenuating actuator is also disclosed. The applications of the solution are somewhat limited, since the measured sound field also comprises sound produced by an actuator.

U.S. Pat. No. 5,018,203 and U.K. Patent Publication Nos. 1 530 814 and 2 160 070 disclose solutions for hearing protectors, in which a sound field is measured and a sound field of opposite sign is produced by a transformer in the hearing protector for attenuating the sound. The supply of an useful signal through a transformer in the hearing protector is also disclosed. By means of hearing protectors, sound entering the ear is attenuated by preventing the penetration of the ambient sound. The applications of the solutions are somewhat limited, and for instance, with these solutions sound cannot be absorbed.

The object of this invention is to provide a method and an apparatus by which it is possible to absorb ambient sound, to produce desired sound, and to produce simultaneously a microphone signal comprising substantially ambient sound only, even though a signal is applied to an actuator for producing sound simultaneously.

The method according to the invention is characterized in that sound is attenuated by absorbing it with an actuator, the effect of a desired value signal on the sound pressure, measured with a sensor, is eliminated.

The apparatus according to the invention is further characterized in that the actuator is arranged to absorb sound, and the apparatus is arranged to eliminate the effect of the desired value signal on the sound pressure, measured with a sensor.

The basic idea of the invention is that a desired value signal is applied to the actuator, which signal the actuator reproduces, and that a sensor measuring sound pressure is attached to the actuator, and that the difference of the sensor signal and the desired value signal is applied as a high gain feedback to the actuator. Then sound not pertaining to the desired value signal is simultaneously absorbed. Further, another basic idea is that the effect of the desired value signal is eliminated from the measured signal, and a microphone signal proportional to a sound not pertaining to the desired value signal is thus produced.

An advantage of the invention is that therewith sound, not pertaining to the desired value signal, can be absorbed in a simple way, and sound in accordance with the desired value sound can be produced simultaneously with the same apparatus, as well as a microphone signal proportional to sound not pertaining to the desired value signal, and all with the same apparatus.

The invention will be described in greater detail in the accompanying details, in which FIG. 1 illustrates schematically a principle of a sound attenuation apparatus, FIG. 2 is a schematic view of a second sound attenuation solution, FIG. 3a is a schematic view of a third sound attenuation solution, FIG. 3b illustrates frequency responses of the solution according to FIG. 3a, FIG. 4 shows a top view of a moving diaphragm of the actuator according to the invention, FIG. 5a is a schematic view of a fourth sound attenuation solution, FIG. 5b illustrates frequency responses of the solution shown in FIG. 5a, FIG. 6 is a schematic view of a fifth sound attenuation solution, FIG. 7 is a schematic side view and cross-section of an actuator, FIG. 8 is a schematic side view and cross-section of another actuator solution, FIGS. 9 to 11 are schematic views of some actuator solutions, FIG. 12 is a schematic view of a solution according to the invention, FIG. 13 is a schematic side view and cross-section of an actuator solution, and FIG. 14 is a schematic side view and cross-section of yet another actuator solution.

FIG. 1 shows a schematic view of the method. The basic unit of the system comprises a planar actuator and a diaphragmatic pressure sensor fastened thereto. The acoustic system of the present invention may simultaneously serve as a noise absorbing and sound reproducing system. The actuator comprises porous stator plates 1, a moving diaphragm 2, 3, a sensor diaphragm 4 that is elastic in thickness direction, a sensor amplifier 8, and a variable gain amplifier A. According to the principle of a feedback system, the sensor signal B equals to the desired value signal I, with the gain of the variable gain amplifier approaching infinite. In practice, with the gain of 20 dB, the difference of the desired value signal and the sensor signal is 1 percent. If the desired value signal is set zero, the sensor signal is also close to zero, which means that the system keeps the sound pressure zero behind an absorbing layer 6, the particle velocity having the maximum value in the absorbing layer, and as a consequence the system also absorbs low frequencies efficiently. In this case the system serves as a sound attenuator known per se. However, the desired value signal 1, can be applied to the system simultaneously, which signal the actuator reproduces. Thus the system can absorb all sound or noise not pertaining to the desired value signal, and can simultaneously reproduce sound of the desired value signal accurately. FIG. 1 also illustrates the securing of an element to the wall 7 by means of an absorbing material 5.

Since the absorbing layer also attenuates the produced sound, it is advantageous to perform correction of the frequency response on the side of the desired value signal, in a unit F(I) shown in FIG. 2. In order that the sensor signal can be differentiated from the desired value signal, the desired value signal is amplified with gain A' equal to gain A, which signal is subtracted from the output signal of the amplifier A. In this way is produced a microphone signal B'=−BA, which is proportional to the sensor signal, the microphone signal consisting only of sound or vibration signal not pertaining to the desired value signal, and applicable to the control of great acoustic systems or to signal traffic between a plurality of elements, for instance, in such a way that elements placed in different rooms constitute an intercom system.

FIG. 3a illustrates a control system, where feedback functions most efficiently on low and medium frequencies, which becomes clear from the frequency responses shown in FIG. 3b. In order that the acoustic power of the elements can be distributed evenly, it is advantageous to adjust the active surface of the moving diaphragm 2 by removing metal-coating from points 10, as shown in FIG. 4, the points forming a raster pattern of a desired shape and providing a desired sound field. In order that high feedback gain can be achieved, it is advantageous to place the pressure sensor as close to the moving diaphragm as possible, and in a point where high frequencies have the least amplitude, such as the point where the diaphragm is secured to the porous stator plates.

FIG. 5a illustrates an embodiment in which feedback gain can be further increased. An electrode 11, producing a signal corresponding to the diaphragm movement, is placed in the moving diaphragm. This signal constitutes an inner quick feedback loop. The gain of the pressure feedback loop is constant between time constants T1 and T2, as shown in FIG. 5b. At the time constant T2, the integration of the pressure loop is started, and correspondingly is started the derivation of the movement feedback, which is finished at the time constant T3, where the gain is as high as in the pressure loop.

A very advantageous embodiment, where a pressure sensor 4 is attached to a moving electret diaphragm 2, is shown in FIG. 6. In this case both the amplitude and the frequency responses of the actuator can be linearized. FIG. 7 illustrates the shape of a porous stator plate with protrusions 11 and an air gap 14 narrowing towards the edges. The stator plates may be produced of plastic powder or plastic fibers by sintering, and they are metallized at least on inner surfaces by vacuum evaporation.

FIG. 8 illustrates an actuator element whose frame has gaps to provide resonators on low frequencies. A back plate 7 and the actuator element 1, 2, 3 may also produce resonances on different frequencies, when pressure feedback automatically adjusts their amplitudes to the level of the desired value. Thus the efficiency of the element can be significantly increased on low frequencies.

Figure 1:
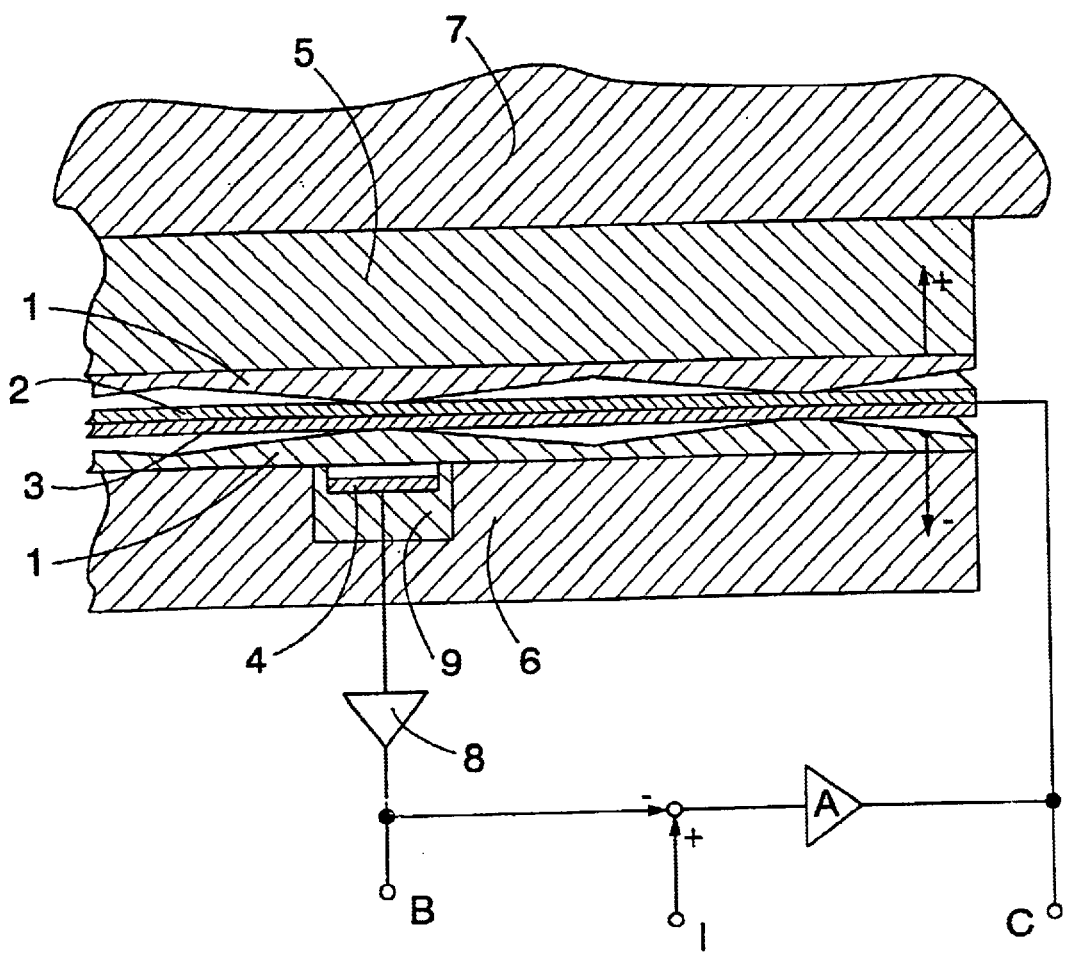
Figure 2:
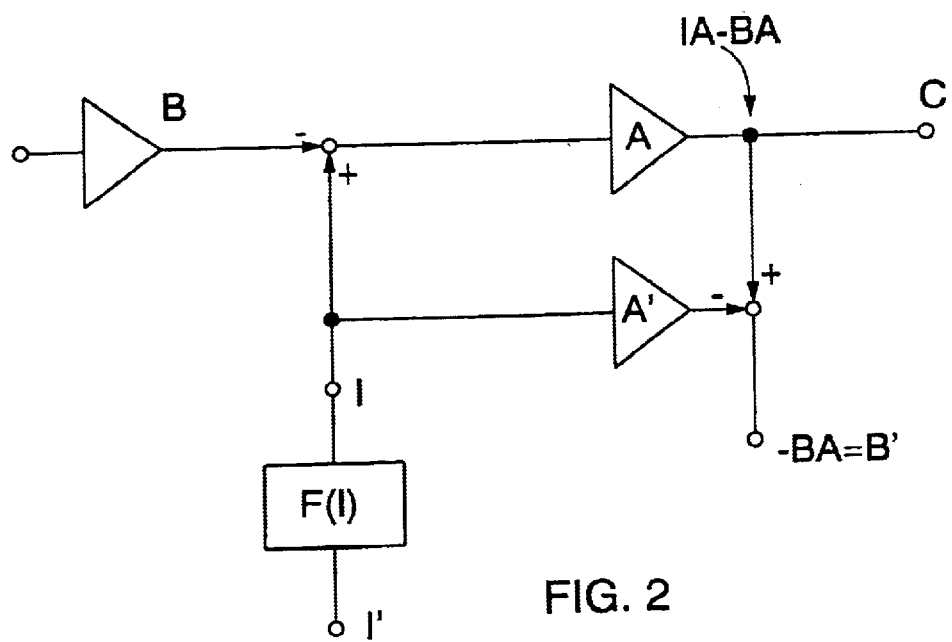
Figure 3A:
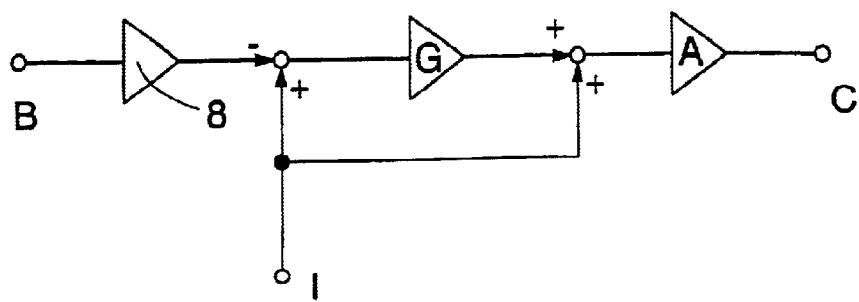
Figure 3B:
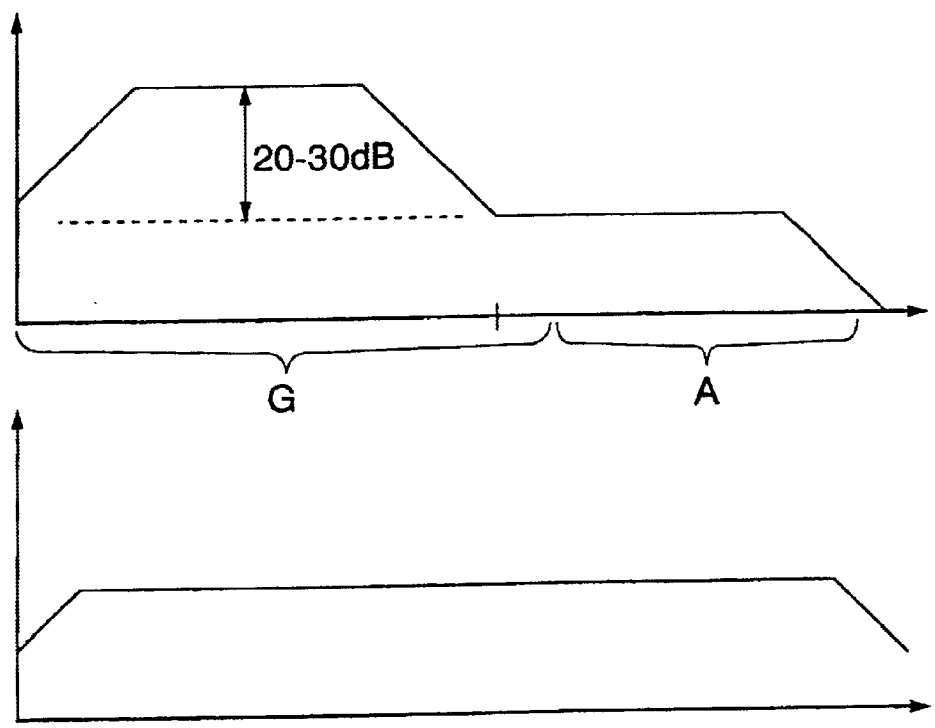
Figure 4:
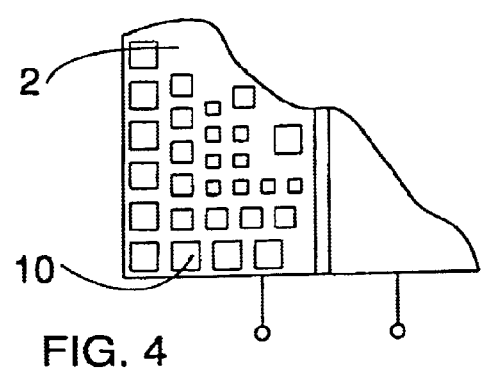
Figure 5A:
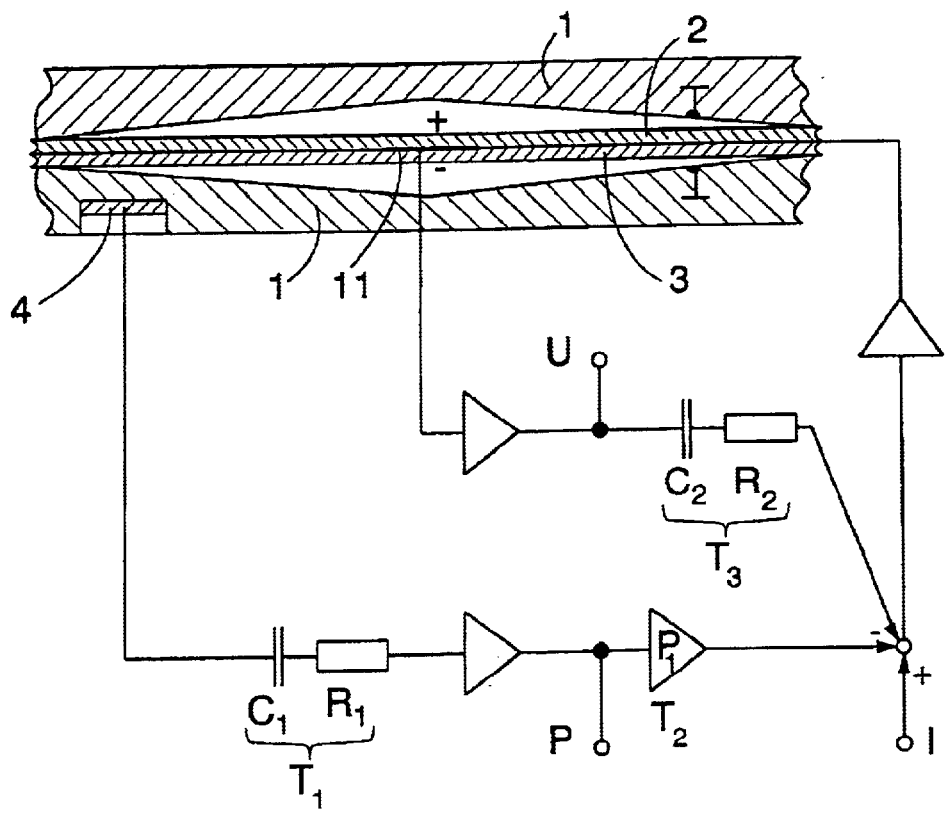
Figure 5B:
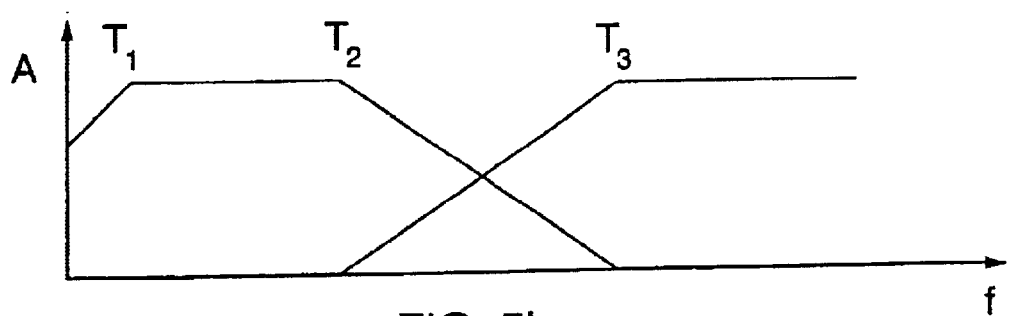
Figure 6:
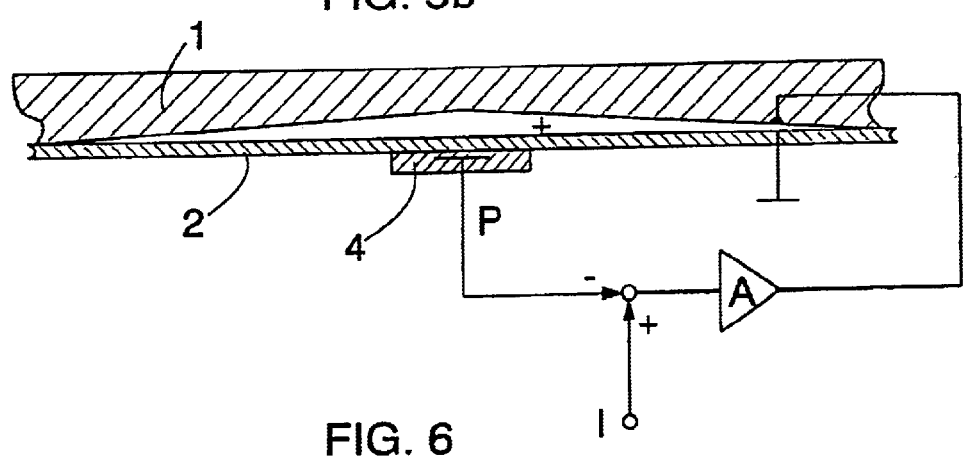
Figure 7:
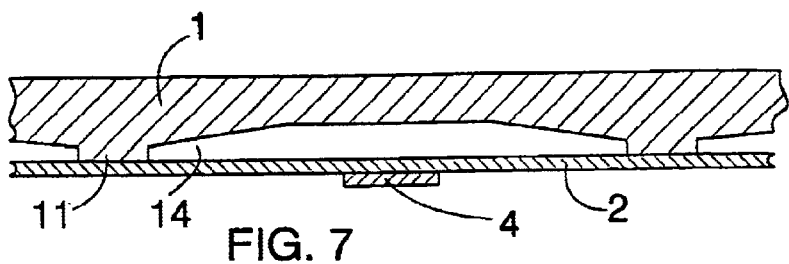
Figure 8:
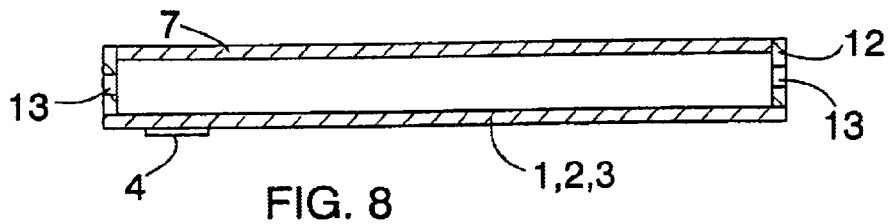
Figure 9:
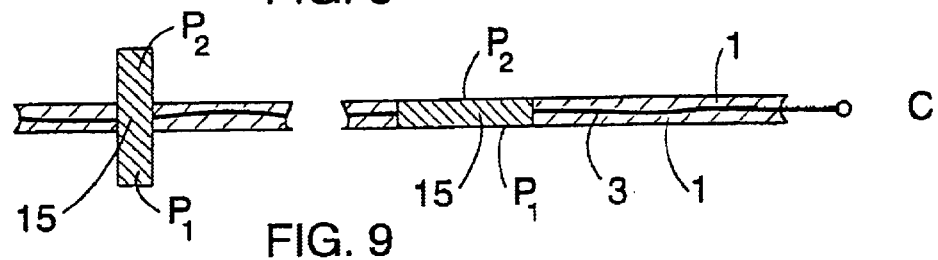
FIG. 9 illustrates an embodiment of the invention, in which pressure sensors $P_1$ and $P_2$ are placed on both sides of the actuator and all the control electronics are connected with the sensors in the same micro circuit in the middle of the actuator.
Figure 10:
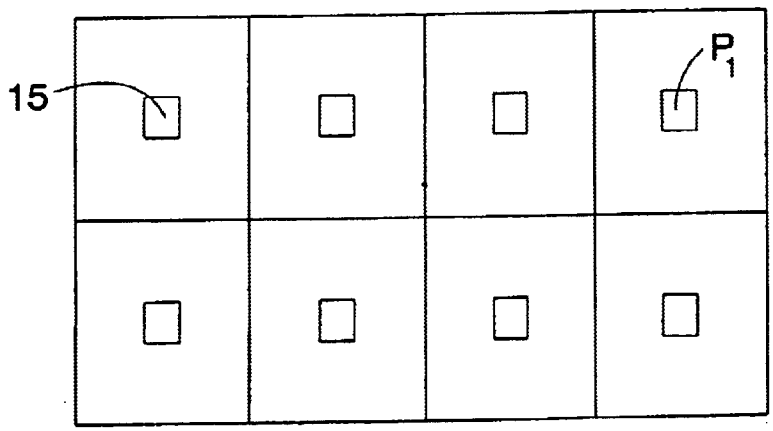
FIG. 10 illustrates an element consisting of modules, in which the micro circuits 15 are shown.
Figure 11:
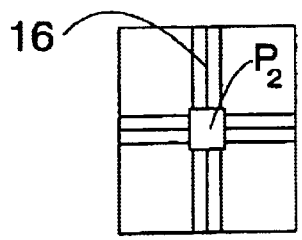

FIG. 11 illustrates a module, on one side of which are shown connecting conductors 16 between modules for transferring supply voltages and signals between modules. The modules may also be cylindrical, in which case they are well suited for the sound attenuation of air conditioners. Conic modules are suited for nozzles of air conditioners. The modules may also be freely shapeable for a purpose.

Figure 12:
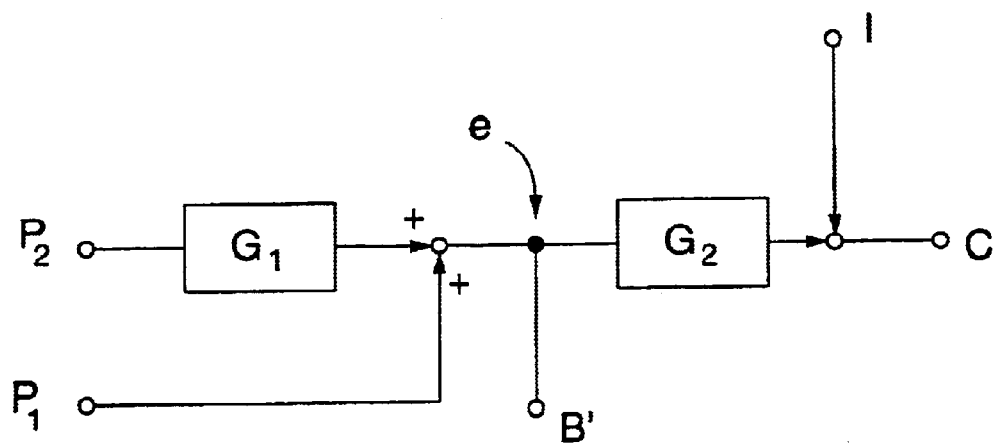

FIG. 12 illustrates a control system where the signal sum of pressure sensors, placed on both sides of the dipole actuator, controls the particle velocity provided by the actuator. The system may be tuned in by applying a signal to the actuator on the frequency band whose absorption is desired or whose sound propagation needs to be prevented. The terminal C is detached and a transfer function $G_1$ is adjusted with a difference e being zero. Since the pressure sensors $P_1$ and $P_2$ on different sides (of the actuator), in practice, are in acoustically different spaces, a transfer function $G_1$ is required for equalizing the signals, and by summing up the signals of the pressure sensors $P_1$ and $P_2$ a microphone signal B', proportional to the ambient sound, can be produced. Thereafter the terminal C is coupled to the actuator and a transfer function $G_2$ is tuned in, so that the desired absorption or attenuation is achieved. An audio signal may be applied to the terminal I. This application has the notable advantage that the actuator control does not appear at all in the difference e, and thus the system is not liable to unstability. Further, in the difference e appears the effect of the ambient sound, in which case a microphone signal B', proportional to the ambient sound, can be produced at the point in question. Only the sum of the pressures $P_1$ and $P_2$, i.e. the ambient sound controls the particle velocity provided by the actuator in the desired manner, since the sound pressure produced by the moving diaphragm of the dipole actuator has an equal effect, but of opposite sign, on the pressure sensors, and as a consequence the sum of the sound pressure signals, produced by the actuator, is zero, if the equalization is performed with the transfer function $G_1$.

Figure 13:
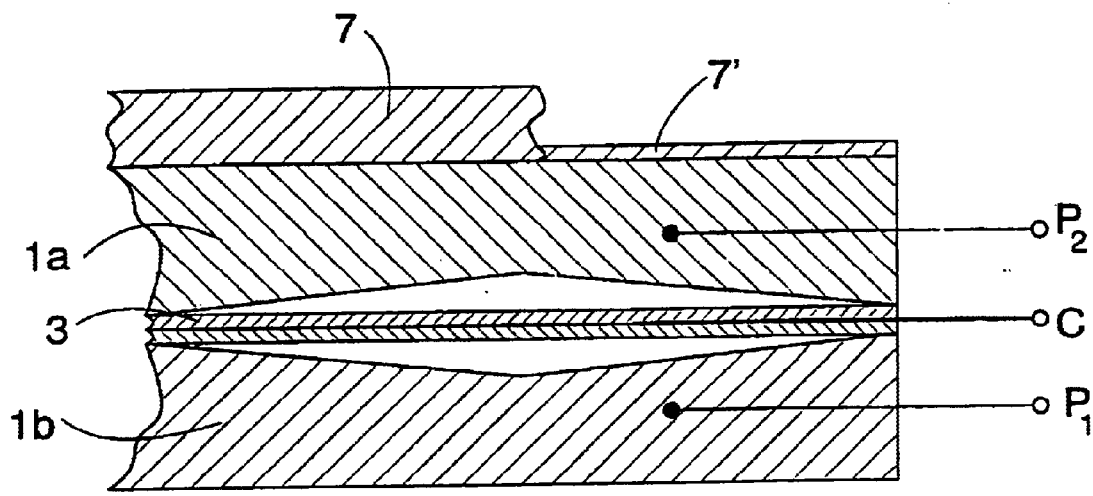

The control system illustrated in FIG. 12 can be applied to the actuator element shown in FIG. 13, close to which element there is a wall or a wall-like structure, or whose one surface is impermeable to air 7'. The tuning of this system is in principle similar to the above in such a way that, in this case, the transfer function $G_1$ is at least derivative. By designing optimally elasticity, air capacity, mass and porosity of the actuator stator plate or the absorption layer behind it, an element can be provided, which has no particle velocity or sound pressure on the surface 7 or 7', when controlling the actuator.

Figure 14:
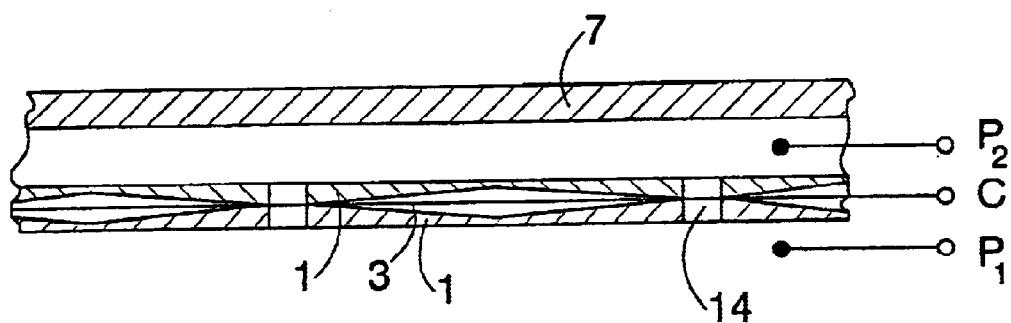

In the arrangement of FIG. 14 the second pressure sensor $P_2$ is placed in an air space, that is at least partially closed, on one side of the dipole actuator. The actuator may also have apertures 14 at the securing points of the moving diaphragm 3. The apertures 14 may be rather close to one another, for instance at a five-centimeter distance from one another. The apertures 14 together with the air space form resonators. In such a case that at least one pressure sensor $P_1$ or $P_2$ is placed in a space that is not closed, the ambient sound can be attenuated by absorption, or the actuator may be placed on the side of an air-conditioning duct and the apparatus absorbs, for instance, interfering noise caused by the air flowing in the duct.

The drawings and the description related thereto are only intended to illustrate the idea of the invention. The invention may vary in details within the scope of the claims.

What is claimed is:

1. A method for processing sound, in which method a desired value signal is supplied to an actuator; the pressure of ambient sound is measured with a sensor attached to the actuator; a difference of the sensor signal and the desired value signal is supplied to the actuator, and sound is produced in accordance with the desired value signal while ambient sound not pertaining to the desired value signal is simultaneously attenuated, wherein:

the actuator is a dipole actuator;

the ambient sound pressure is measured by pressure sensors on both sides of the dipole actuator;

the signal of at least one of the pressure sensors is adjusted with a transfer function to the effect that when summing the signals of the pressure sensors, the sound pressure caused by the actuator is cancelled out, and a microphone signal proportional to the ambient sound is produced.

2. A method as claimed in claim 1, wherein on one side of the dipole actuator there is at least partly closed air space where the second pressure sensor is placed.

3. A method as claimed in claim 2, wherein the signal of the sensor placed in the closed air space is derivated.

4. A method as claimed in claim 1, wherein a microphone signal proportional only to the ambient sound is produced.

5. A method as claimed in claim 4, wherein from an output signal of a variable gain amplifier is subtracted the desired value signal amplified by gain that equals to the gain of the variable gain amplifier, when the obtained signal corresponds to the microphone signal proportional to the ambient sound.

6. A method as claimed in claim 4, wherein the microphone signal, proportional to the ambient sound, is applied as a desired value signal to the other element.

7. A method as claimed in claim 1, wherein the actuator has at least one moving diaphragm whose kinetic velocity is measured, and an inner quick feedback loop is formed of this kinetic velocity.

8. An apparatus for sound processing comprising an acoustic actuator, a sensor attached thereto for measuring sound pressure, means for applying a desired value signal to the actuator, and means for applying to the actuator the difference between the sound pressure measured with the sensor and the desired value signal, wherein:

the actuator is a dipole actuator, that is arranged to absorb sound;

at least two pressure sensors are placed on different sides of the actuator; and the apparatus comprises means for adjusting the signal of at least one of the sensors with a transfer function to the effect that the sound pressure caused by the actuator is cancelled out when the signals of the pressure sensors are summed, eliminating the effect of the desired value signal on the sound pressure measured with the sensor.

9. An apparatus as claimed in claim 8, wherein on one side of the dipole actuator there is at least partly closed air space where the second pressure sensor is.

10. An apparatus as claimed in claim 8, wherein the apparatus is arranged to produce a microphone signal proportional to the ambient sound.

11. An apparatus as claimed in claim 10, wherein the apparatus comprises means for subtracting the desired value signal from the sound pressure measured with the sensor, in order to produce the microphone signal proportional to the ambient sound.

12. An apparatus as claimed in claim 8, wherein at least on one surface of the actuator there is additional sound absorbing material, thicker than the porous stator plate.

13. An apparatus as claimed in claim 8, wherein at least two actuator elements are positioned facing each other as a mirror image.

14. An apparatus as claimed in claim 8, wherein an electronic unit controlling the elements is placed at the edge of each element.

15. An apparatus as claimed in claim 8, wherein the actuator has a moving diaphragm and an electrode associated with the moving diaphragm is raster patterned in order for distributing the power optimally.

16. An apparatus as claimed in claim 8, wherein a pressure sensor is attached to a moving diaphragm on the actuator.

17. An apparatus as claimed in claim 8, wherein the actuator comprises a porous stator plate that is metallized at least on the inner surface, an electret diaphragm, and a pressure sensor.

18. An apparatus as claimed in claim 8, wherein the actuator comprises bordering frames with apertures and a back plate, and the apertures, the back plate of the actuator and/or the actuator constitute resonators.

19. An apparatus as claimed in claim 9, wherein on one side of the actuator there is elastic, air containing, porous material, on the reverse side of which there is a layer impermeable to air or little permeable to air.

* * * * *